(12) United States Patent
Lin et al.

(10) Patent No.: US 7,569,704 B1
(45) Date of Patent: Aug. 4, 2009

(54) DYE COMPOUND

(75) Inventors: Jiann-T'suen Lin, Taipei (TW);
Yung-Sheng Yen, Taipei (TW);
Ying-Chan Hsu, Taipei (TW);
Ta-Chung Yin, Taoyuan Hsien (TW)

(73) Assignees: Everlight USA, Inc., Pineville, NC (US); Academia Sinica, Taipei (TW)

( * ) Notice: Subject to any disclaimer, the term of this patent is extended or adjusted under 35 U.S.C. 154(b) by 0 days.

(21) Appl. No.: 12/155,033

(22) Filed: May 29, 2008

(30) Foreign Application Priority Data

Apr. 7, 2008 (TW) .............................. 97112471 A

(51) Int. Cl.
*C07D 409/04* (2006.01)
*C07D 409/14* (2006.01)

(52) U.S. Cl. ..................... 548/442; 548/527; 548/560

(58) Field of Classification Search .................. None
See application file for complete search history.

(56) References Cited

U.S. PATENT DOCUMENTS

| | | | | |
|---|---|---|---|---|
| 7,446,207 | B2 * | 11/2008 | Velusamy et al. | ............ 548/134 |
| 2006/0130249 | A1 * | 6/2006 | Ikeda et al. | .................... 8/550 |
| 2007/0240756 | A1 * | 10/2007 | Lee et al. | .................. 136/252 |

FOREIGN PATENT DOCUMENTS

JP      2003-282165    * 10/2003
WO    WO 2007/100033   * 9/2007
WO    WO 2008/004580   * 1/2008

OTHER PUBLICATIONS

Kim et al., "Molecular Engineering of Organic Sensitizers for Solar Cell Applications", Journal of the American Chemical Society, 128(51), 16701-16707, 2006.*

* cited by examiner

*Primary Examiner*—Fiona T Powers
(74) *Attorney, Agent, or Firm*—Bacon & Thomas, PLLC

(57) ABSTRACT

The present invention relates to a novel dye compound, represented by the following formula (I):

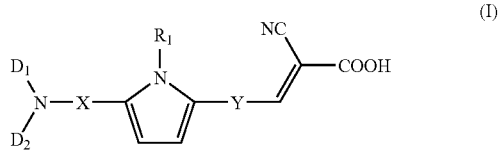

wherein $R_1$, $D_1$, $D_2$, X, and Y are defined the same as the specification. The dye compound of the present invention is suitable for Dye-Sensitized Solar Cell (DSSC). In addition, the dye compound of the present invention has high molar absorption coefficient, so that the DSSC manufactured by the dye compound of the present invention can have good photoelectric characteristics.

17 Claims, No Drawings

DYE COMPOUND

BACKGROUND OF THE INVENTION

1. Field of the Invention

The present invention relates to a dye compound and, more particularly, to a dye compound which is used for the dye-sensitized solar cell (DSSC).

2. Description of Related Art

With the development of industrial technology, the serious problems the whole world is facing today are the energy crisis and the environmental pollution. In order to solve the global energy crisis and to reduce the environmental pollution, one of the effective means is the solar cell, which can convert the solar energy into the electricity. Since the dye-sensitized solar cell has the advantages of low manufacturing cost, large-scale production, great flexibility, light transmittance, and being capable of use in the buildings, the application of the dye-sensitized solar cell becomes more and more attractive.

Currently, Grätzel et al. have disclosed a series of literatures, for example, O'Regan, B.; Grätzel, M. *Nature* 1991, 353, 737, which show the practicability of the dye-sensitized solar cell. The general structure of the dye-sensitized solar cell comprises an anode, a cathode, a nano-porous titanium dioxide layer, a dye, and electrolyte, wherein the dye plays a critical role in the conversion efficiency of the dye-sensitized solar cell. The dye suitable for the dye-sensitized solar cell must have characteristics in broad absorption spectrum, high molar absorption coefficient, thermal stability, and light stability.

Grätzel's lab has published a serious of ruthenium complexes as the dyes for the dye-sensitized solar cell. Grätzel's lab published a dye-sensitized solar cell prepared with a N3 dye in 1993, and the conversion efficiency of the dye-sensitized solar cell is 10.0% under the illumination of AM 1.5 stimulated light. The incident photon-to-current conversion efficiency (IPCE) value of the N3 dye is 80% in the range of 400 to 600 nm. Although hundreds of dye complexes have developed, the conversion efficiency of those dye complexes is not as good as the N3 dye. The structure of the N3 dye is represented by the following formula (a).

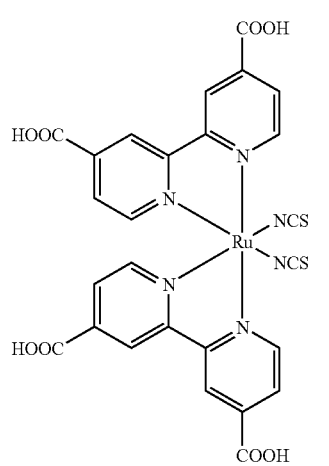

In 2003, Grätzel's lab published a dye-sensitized solar cell prepared with a N719 dye, and the conversion efficiency of the dye-sensitized solar cell is improved to 10.85% under the illumination of AM 1.5 stimulated light, wherein the structure of the N719 dye is represented by the following formula (b).

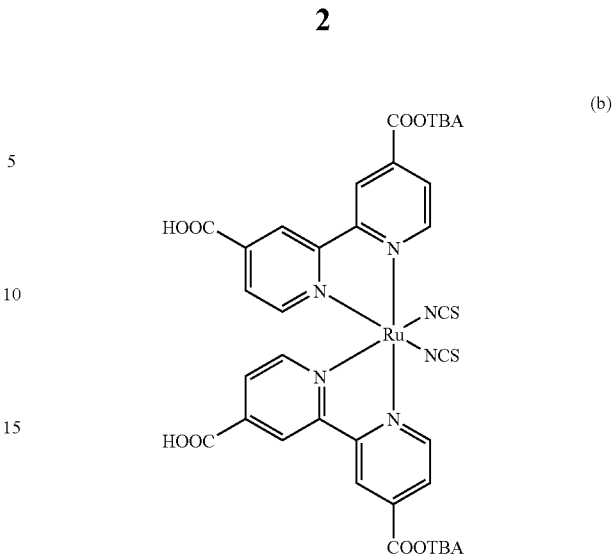

Grätzel's lab also published a dye-sensitized solar cell prepared with a black dye in 2004, and the conversion efficiency of the dye-sensitized solar cell is 11.04% under the illumination of AM 1.5 stimulated light. The black dye can enhance the spectral response in red and near-IR region, so the conversion efficiency of the dye-sensitized solar cell can be improved. The structure of the black dye is represented by the following formula (c).

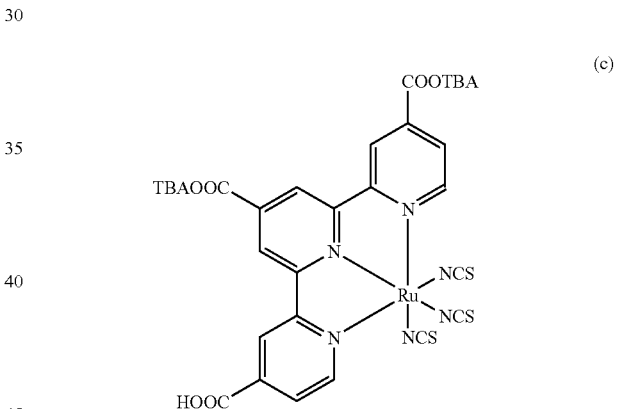

In addition to the ruthenium complexes such as the N3 dye, the N719 dye, and the black dye, other types of dye compounds, which can be used in the dye-sensitized solar cell, are platinum complexes, osmium complexes, iron complexes, and copper complexes. However, the results of various researches show that the conversion efficiency of the ruthenium complexes is still better than other types of dye compounds.

The ruthenium complexes are the sensitizer dyes with the highest conversion efficiency nowadays. However, the manufacturing cost of the ruthenium complexes is high, and there may be problems of short supply when the ruthenium complexes are used widely. The organic sensitizers for the dye-sensitized solar cell have advantages of high molar absorption coefficient. Besides, it is possible to produce various organic sensitizers through molecular design. Hence, dye-sensitized solar cells with different colors can be manufactured to improve the application flexibility of the dye-sensitized solar cells. In addition, it is also possible to change the color of the dye-sensitized solar cell to match with the color of objects. Currently, dye derivatives, such as coumarin (Hara, K.;

Sayama, K.; Arakawa, H.; Ohga, Y.; Shinpo, A.; Sug, S. *Chem. Commun.*, 2001, 569), indoline (Horiuchi, T.; Miura, H.; Sumioka, K.; Uchida, S. *J. Am. Chem. Soc.*, 2004, 126 (39), 12218), and merocyanine (Otaka, H.; Kira, M.; Yano, K.; Ito, S.; Mitekura, H.; Kawata, T.; Matsui, F. *J. Photochem. Photobiol. A: Chem.*; 2004, 164, 67), have already applied in the manufacture of dye-sensitized solar cells.

The dyes for the dye-sensitized solar cell influence the conversion efficiency greatly. Hence, it is desirable to provide a dye compound, which can improve the conversion efficiency of the dye-sensitized solar cell.

SUMMARY OF THE INVENTION

The present invention is to provide a novel dye compound, which is used for a dye-sensitized solar cell. The dye compound of the present invention has high molar absorption coefficient. Hence, the dye-sensitized solar cell, which is prepared with the novel dye of the present invention, has excellent photoelectric property.

The dye compound of the present invention can be represented by the following formula (I):

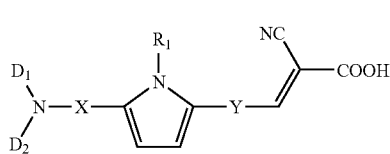

(I)

wherein $R_1$ is $C_{1\sim6}$ alkyl;

$D_1$, and $D_2$ are each independently $C_{1\sim6}$ alkyl

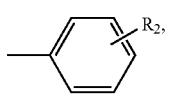

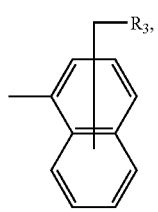

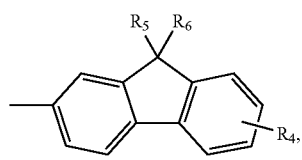

or

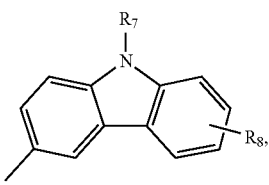

wherein $R_2$, $R_3$, $R_4$, and $R_8$ are each independently H, $C_{1\sim6}$ alkyl, $C_{1\sim6}$ alkoxy, amino, or halogen, $R_5$, and $R_6$ are each independently H, $C_{1\sim6}$ alkyl, $C_{1\sim6}$ alkoxy, or halogen, and $R_7$ is H, or $C_{1\sim6}$ alkyl;

X is

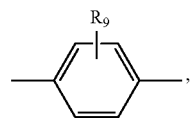

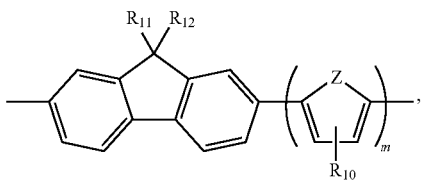

or

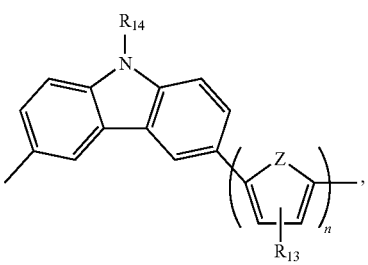

wherein $R_9$, $R_{11}$, and $R_{12}$ are each independently H, $C_{1\sim6}$ alkyl, $C_{1\sim6}$ alkoxy, or halogen, $R_{10}$, $R_{13}$, and $R_{14}$ are each independently H, or $C_{1\sim6}$ alkyl, Z is O, S, or Se, m is 0, or 1, and n is 0, or 1;

Y is

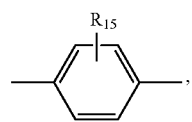

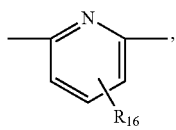

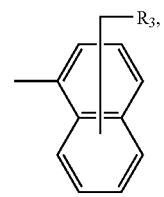

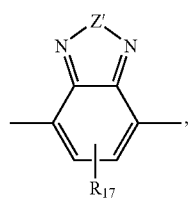

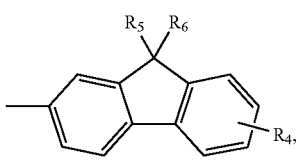

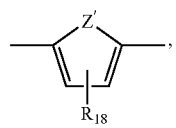

or

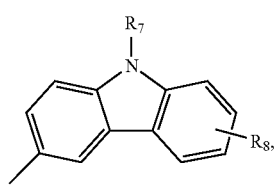

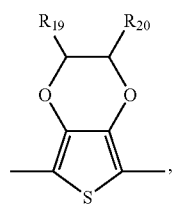

wherein $R_2$, $R_3$, $R_4$, and $R_8$ are each independently H, $C_{1\sim6}$ alkyl, $C_{1\sim6}$ alkoxy, amino, or halogen, $R_5$, and $R_6$ are each independently H, $C_{1\sim6}$ alkyl, $C_{1\sim6}$ alkoxy, or halogen, and $R_7$ is H or $C_{1\sim6}$ alkyl. Preferably, $D_1$, and $D_2$ are each independently

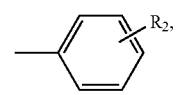

or

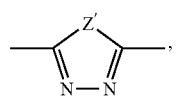

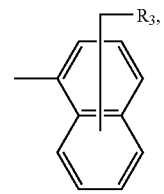

wherein $R_{15}$, $R_{16}$, and $R_{17}$ are each independently H, $C_{1\sim6}$ alkyl, $C_{1\sim6}$ alkoxy, or halogen, $R_{18}$, $R_{19}$, and $R_{20}$ are each independently H, or $C_{1\sim6}$ alkyl, and Z' is O, S, or Se.

In the above formula (I), $R_1$ may be $C_{1\sim6}$ alkyl. Preferably, $R_1$ is —$CH_3$ or —$C_2H_5$. More preferably, $R_1$ is —$CH_3$.

In the above formula (I), $D_1$, and $D_2$ may be each independently $C_{1\sim6}$ alkyl,

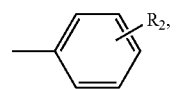

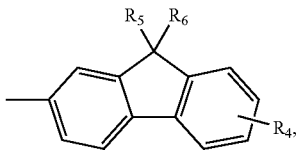

or

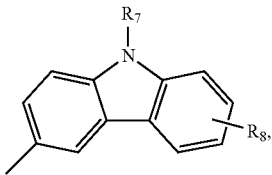

wherein $R_2$, $R_3$, $R_4$, and $R_8$ are each independently H, $C_{1\sim6}$ alkyl, $C_{1\sim6}$ alkoxy, amino, or halogen, $R_5$ and $R_6$ are each independently H, $C_{1\sim6}$ alkyl, $C_{1\sim6}$ alkoxy, or halogen, and $R_7$ is H or $C_{1\sim6}$ alkyl. More preferably, $D_1$ and $D_2$ are each independently

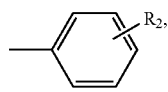

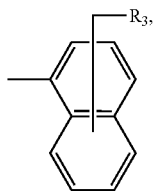

or

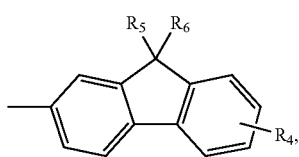

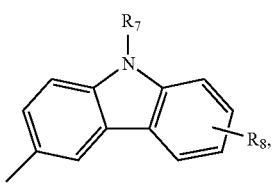

wherein $R_2$, $R_3$, $R_4$, $R_5$, $R_6$, and $R_8$ are each independently H, $C_{1\sim6}$ alkyl, $C_{1\sim6}$ alkoxy, or halogen, and $R_7$ is H or $C_{1\sim6}$ alkyl. Most preferably, $D_1$ and $D_2$ are each independently

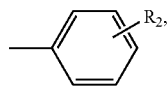

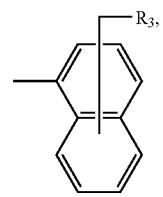

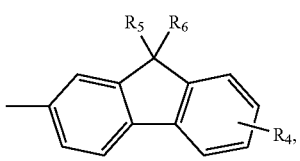

or

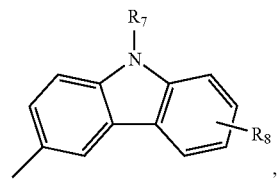

wherein $R_2$, $R_3$, $R_4$, $R_5$, $R_6$, $R_7$, and $R_8$ are each independently H, or $C_{1\sim6}$ alkyl.

In addition, in one aspect of the present invention, the $D_1$ and $D_2$ in the above formula (I) can be each independently

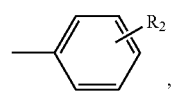

or

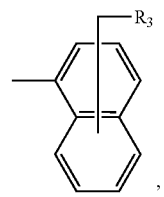

wherein $R_2$ and $R_3$ are each independently H, $C_{1\sim6}$ alkyl, $C_{1\sim6}$ alkoxy, amino, or halogen. Preferably, $R_2$ and $R_3$ in $D_1$ and $D_2$ is H, or $C_{1\sim6}$ alkyl. More preferably, $R_2$ and $R_3$ in $D_1$ and $D_2$ is H.

In the above formula (I), X may be

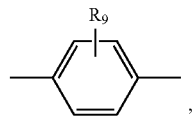

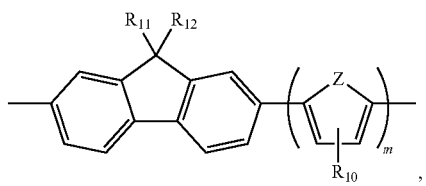

or

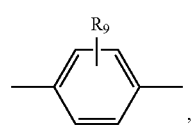

wherein $R_9$, $R_{11}$, and $R_{12}$ are each independently H, $C_{1\sim 6}$ alkyl, $C_{1\sim 6}$ alkoxy, or halogen, $R_{10}$, $R_{13}$, and $R_{14}$ are each independently H, or $C_{1\sim 6}$ alkyl, Z is O, S, or Se, m is 0 or 1, and n is 0 or 1. Preferably, X is

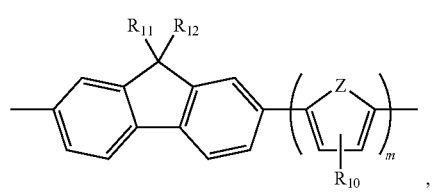

or

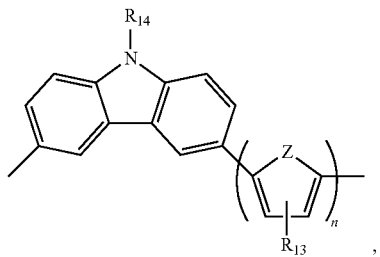

wherein $R_9$, $R_{11}$, and $R_{12}$ are each independently H, $C_{1\sim 6}$ alkyl, $C_{1\sim 6}$ alkoxy, or halogen, $R_{10}$, $R_{13}$, and $R_{14}$ are each independently H or $C_{1\sim 6}$ alkyl, Z is S, m is 0 or 1, and n is 0 or 1. More preferably, X is

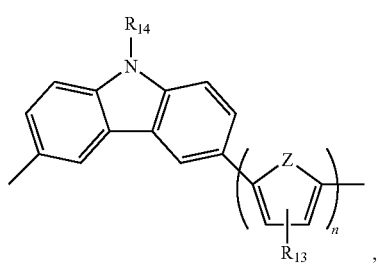

or

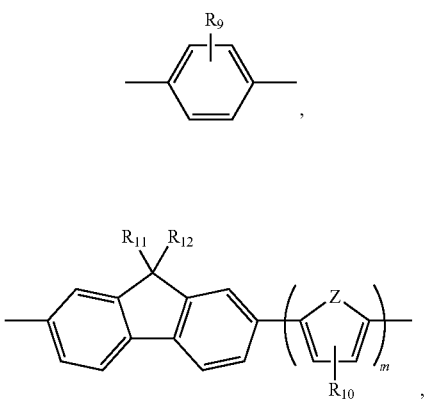

wherein $R_9$, $R_{11}$, and $R_{12}$ are each independently H, $C_{1\sim 6}$ alkyl, $C_{1\sim 6}$ alkoxy, or halogen, $R_{10}$, $R_{13}$, and $R_{14}$ are each independently H, or $C_{1\sim 6}$ alkyl, Z is S, m is 0 or 1, and n is 0. Most preferably, X is

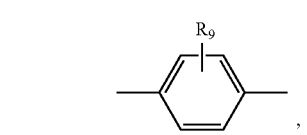

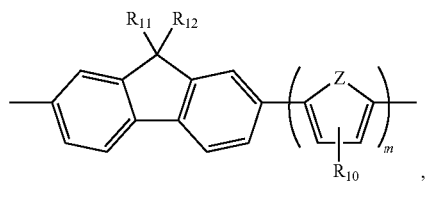

or

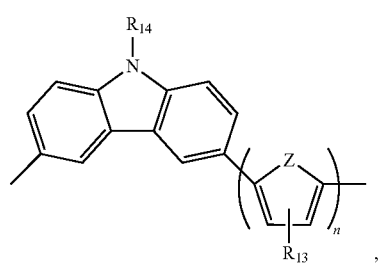

wherein $R_9$, $R_{10}$, $R_{11}$, $R_{12}$, $R_{13}$, and $R_{14}$ are each independently H, or $C_{1\sim6}$ alkyl, Z is S, m is 0 or 1, and n is 0.

In the above formula (I), Y may be

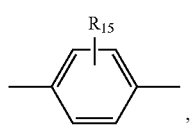

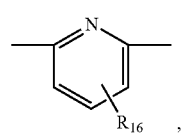

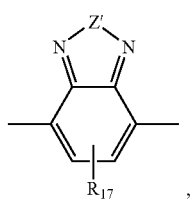

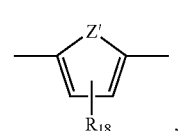

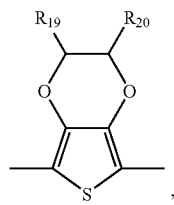

or

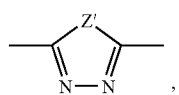

wherein $R_{15}$, $R_{16}$, and $R_{17}$ are each independently H, $C_{1\sim6}$ alkyl, $C_{1\sim6}$ alkoxy, or halogen, $R_{18}$, $R_{19}$, and $R_{20}$ are each independently H or $C_{1\sim6}$ alkyl, and Z' is O, S, or Se. Preferably, Y is

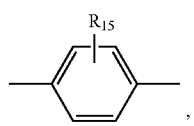

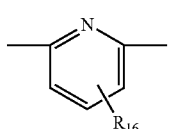

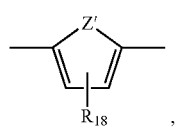

or

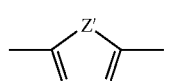

wherein $R_{15}$, and $R_{16}$ are each independently H, $C_{1\sim6}$ alkyl, $C_{1\sim4}$ alkoxy, or halogen, $R_{18}$ is H or $C_{1\sim6}$ alkyl, and Z' is O, S or Se. More preferably, Y is or
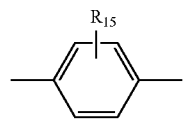
or
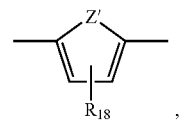,
wherein $R_{15}$ is H, $C_{1\sim6}$ alkyl, $C_{1\sim6}$ alkoxy, or halogen, $R_{18}$ is H or $C_{1\sim6}$ alkyl, and Z' is O, S or Se. Most preferably, Y is
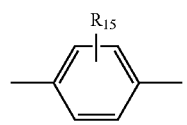
or
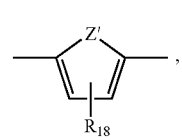,
wherein $R_{15}$ is H, $C_{1\sim6}$ alkyl, $C_{1\sim6}$ alkoxy, or halogen, $R_{18}$ is H or $C_{1\sim6}$ alkyl, and Z' is O or S. Most preferably, Y is
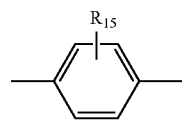
or
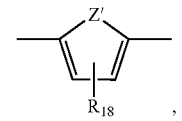,
wherein $R_{15}$ and $R_{18}$ are H, and Z' is S.
The examples of the dye compound presented by the above formula (I) are:
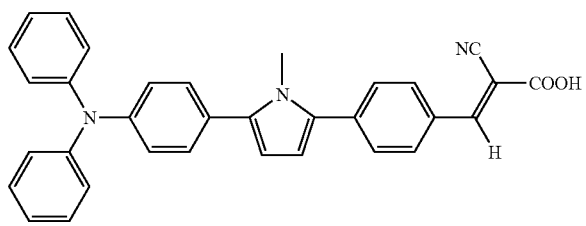
(15a)
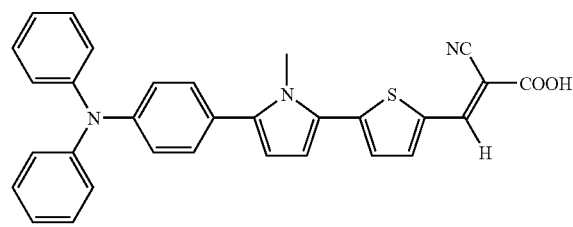
(15b)
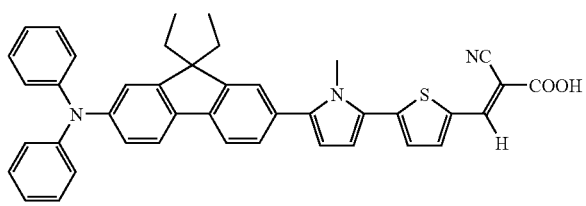
(26a)

-continued

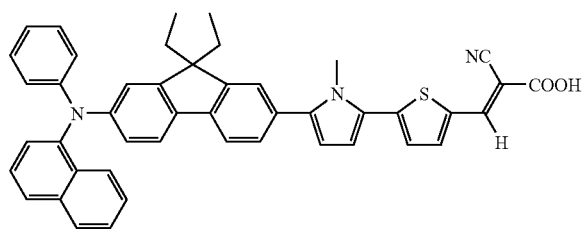
(26b)

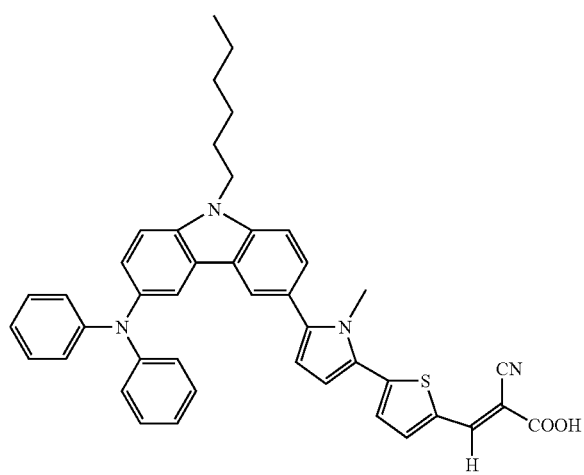
(36)

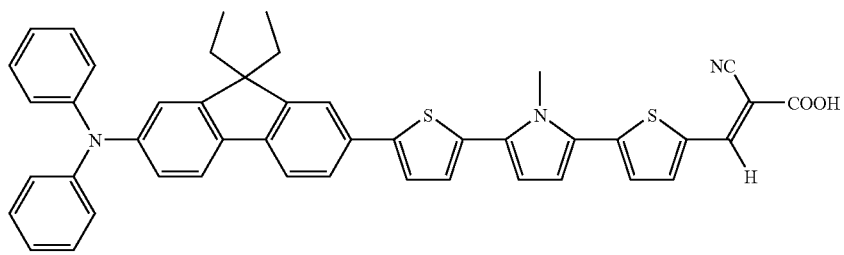
(46)

In the present invention, the molecule of the dye compound is presented in form of free acid. However, the actual form of the dye compound of the present invention may be salt, and more likely, may be alkaline metal salt or quaternary ammonium salt.

In addition, the dye compound of the present invention may be used for a dye of a dye-sensitized solar cell.

Other objects, advantages, and novel features of the invention will become more apparent from the following detailed description

DETAILED DESCRIPTION OF THE PREFERRED EMBODIMENT

A dye compound of the present invention can be prepared by the methods shown in scheme 1 to 4.

[Scheme 1]

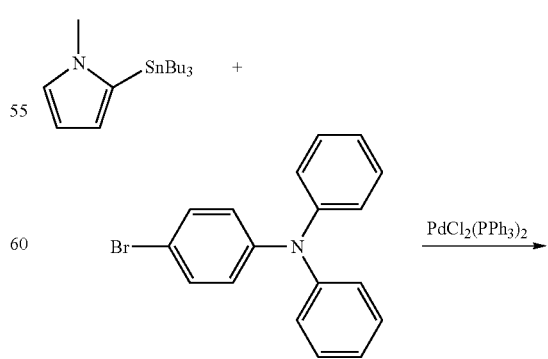

11

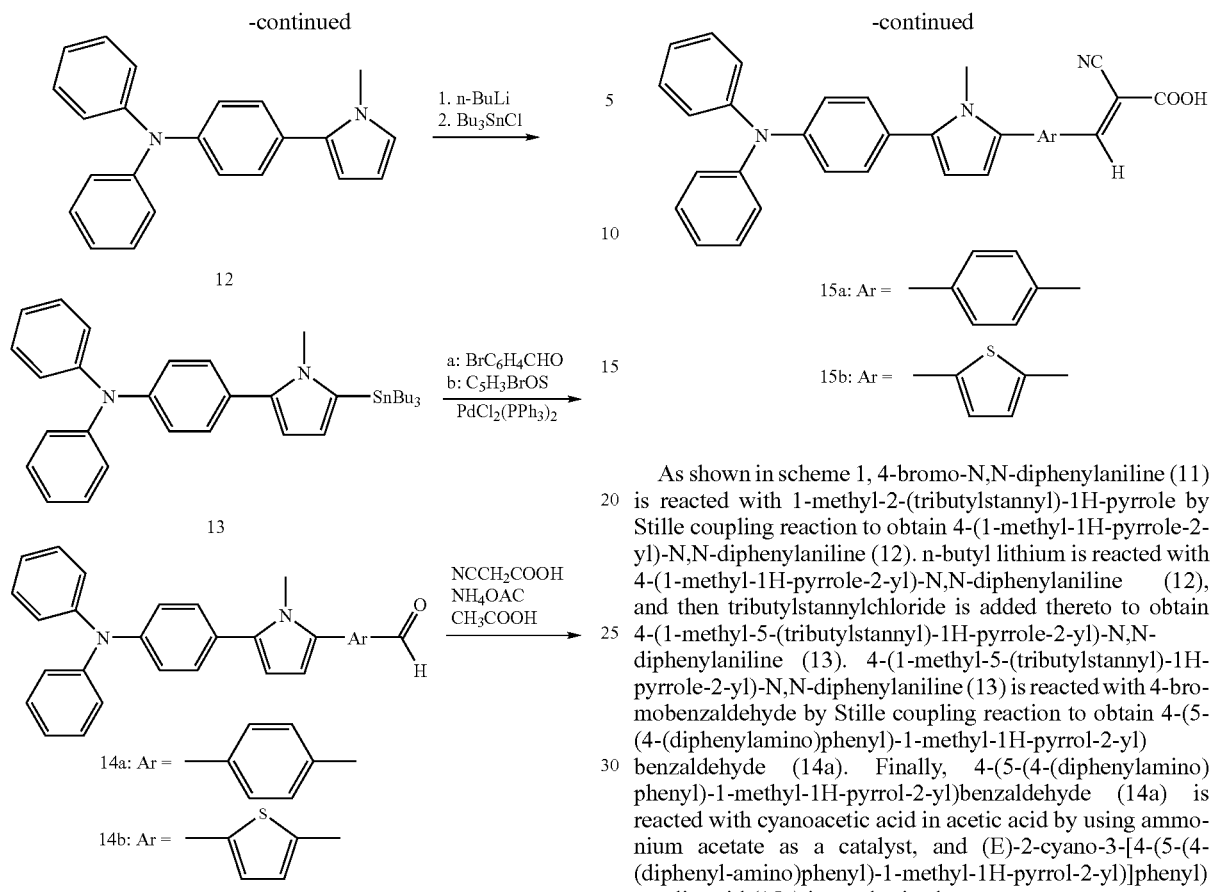

As shown in scheme 1, 4-bromo-N,N-diphenylaniline (11) is reacted with 1-methyl-2-(tributylstannyl)-1H-pyrrole by Stille coupling reaction to obtain 4-(1-methyl-1H-pyrrole-2-yl)-N,N-diphenylaniline (12). n-butyl lithium is reacted with 4-(1-methyl-1H-pyrrole-2-yl)-N,N-diphenylaniline (12), and then tributylstannylchloride is added thereto to obtain 4-(1-methyl-5-(tributylstannyl)-1H-pyrrole-2-yl)-N,N-diphenylaniline (13). 4-(1-methyl-5-(tributylstannyl)-1H-pyrrole-2-yl)-N,N-diphenylaniline (13) is reacted with 4-bromobenzaldehyde by Stille coupling reaction to obtain 4-(5-(4-(diphenylamino)phenyl)-1-methyl-1H-pyrrol-2-yl) benzaldehyde (14a). Finally, 4-(5-(4-(diphenylamino)phenyl)-1-methyl-1H-pyrrol-2-yl)benzaldehyde (14a) is reacted with cyanoacetic acid in acetic acid by using ammonium acetate as a catalyst, and (E)-2-cyano-3-[4-(5-(4-(diphenyl-amino)phenyl)-1-methyl-1H-pyrrol-2-yl)]phenyl) acrylic acid (15a) is synthesized.

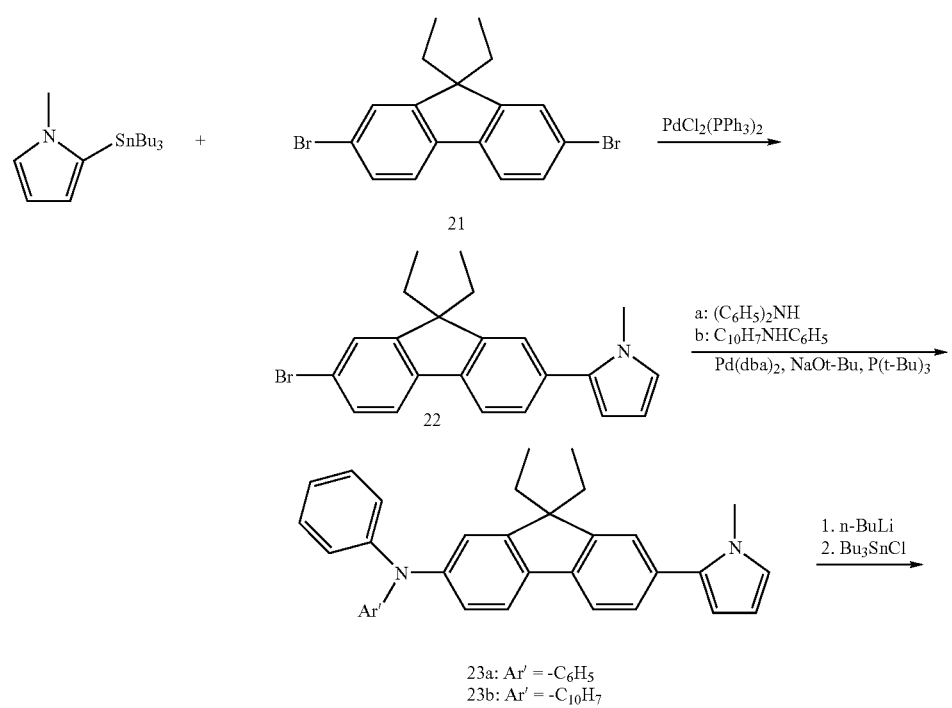

-continued

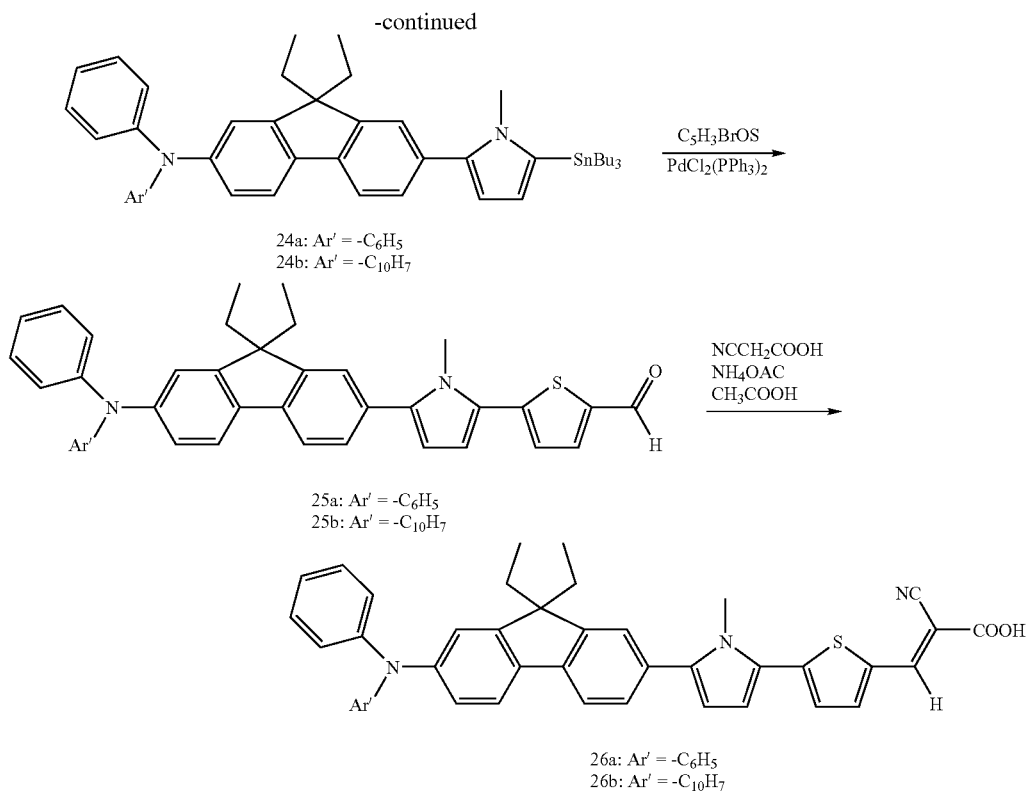

24a: Ar' = -C₆H₅
24b: Ar' = -C₁₀H₇

25a: Ar' = -C₆H₅
25b: Ar' = -C₁₀H₇

26a: Ar' = -C₆H₅
26b: Ar' = -C₁₀H₇

As shown in scheme 2, 2,7-dibromo-9,9-diethyl-9H-fluorene (21) is reacted with 1-methyl-2-(tributylstannyl)-1H-pyrrole by Stille coupling reaction to obtain 2-(7-bromo-9,9-diethyl-9H-fluoren-2-yl)-1-methyl-1H-pyrrole (22). Then, in the presence of sodium tert-butoxide, Pd(dba)$_2$, and tri-tert-butyl phosphine, 2-(7-bromo-9,9-diethyl-9H-fluoren-2-yl)-1-methyl-1H-pyrrole (22) is reacted with diphenylamine to obtain 9,9-diethyl-7-(1-methyl-1H-pyrrol-2-yl)-N,N-diphenyl-9H-fluoren-2-amine (23a). n-butyl lithium is reacted with 9,9-diethyl-7-(1-methyl-1H-pyrrol-2-yl)-N,N-diphenyl-9H-fluoren-2-amine (23a), and then tributylstannylchloride is added thereto to obtain N-methyl-2-(7-diphenyl-amino-9,9-diethyl-9H-fluoren-2-yl)-5-tributylstannylpyrrole (24a). N-methyl-2-(7-diphenylamino-9,9-diethyl-9H-fluoren-2-yl)-5-tributyl-stannylpyrrole (24a) is reacted with 5-bromo-2-thiophene carboxaldehyde by Stille coupling reaction to obtain 5-[N-methyl-2-(7-diphenylamino-9,9-diethyl-9H-fluoren-2-yl)pyrrol-5-yl]thiophene-2-carbaldehyde (25a). Finally, 5-[N-methyl-2-(7-diphenylamino-9,9-diethyl-9H-fluoren-2-yl)pyrrol-5-yl]thiophene-2-carbaldehyde (25a) is reacted with cyanoacetic acid in acetic acid by using ammonium acetate as a catalyst, and (E)-2-cyano-3-[5-(N-methyl-2-(7-diphenylamino-9,9-diethyl-9H-fluoren-2-yl)pyrrol-5-yl)thiophen-2-yl]acrylic acid (26a) is obtained.

[Scheme 3]

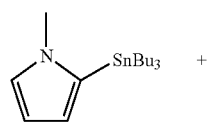 +

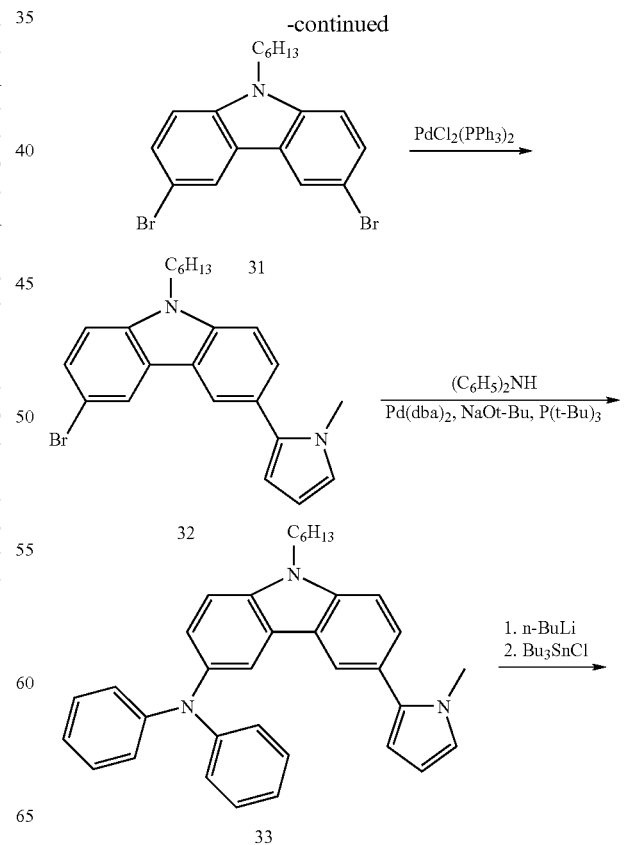

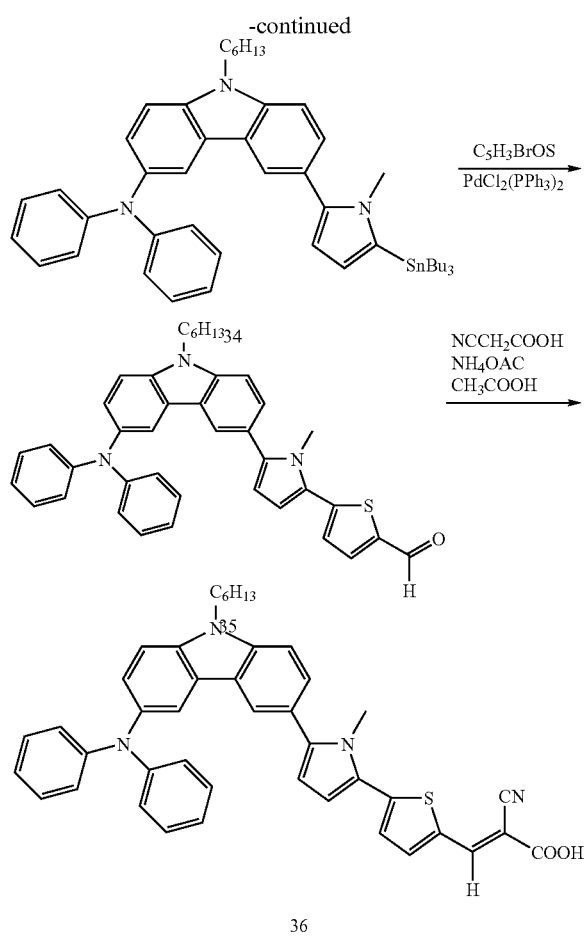

As shown in scheme 3, 3,6-dibromo-9-hexyl-9H-carbazole (31) is reacted with 1-methyl-2-(tributylstannyl)-1H-pyrrole by Stille coupling reaction to obtain N-methyl-2-(3-bromo-9-hexyl-9H-carbazol-6-yl)pyrrole (32). Then, in the presence of sodium tert-butoxide, Pd(dba)$_2$, and tri-tert-butyl phosphine, N-methyl-2-(3-bromo-9-hexyl-9H-carbazol-6-yl)pyrrole (32) is reacted with diphenylamine to obtain N-methyl-2-(3-diphenylamino-9-hexyl-9H-carbazol-6-yl)pyrrole (33). n-butyl lithium is reacted with N-methyl-2-(3-diphenylamino-9-hexyl-9H-carbazol-6-yl)pyrrole (33), and then tributylstannylchloride is added thereto to obtain N-methyl-2-(3-diphenylamino-9-hexyl-9H-carbazol-6-yl)-5-tributylstannylpyrrole (34). N-methyl-2-(3-diphenylamino-9-hexyl-9H-carbazol-6-yl)-5-tributylstannylpyrrole (34) is reacted with 5-bromo-2-thiophene-carboxaldehyde by Stille coupling reaction to obtain 5-[N-methyl-2-(3-diphenylamino-9-hexyl-9H-carbazol-6-yl)pyrrol-5-yl]thiophene-2-carbaldehyde (35). Finally, 5-[N-methyl-2-(3-diphenylamino-9-hexyl-9y-carbazol-6-yl)pyrrol-5-yl]thiophene-2-carbaldehyde (35) is reacted with cyanoacetic acid in acetic acid by using ammonium acetate as a catalyst, and (E)-2-cyano-3-[5-(N-methyl-2-(3-diphenylamino-9-hexyl-9H-carbazol-6-yl)pyrrol-5-yl)thiophen-2-yl]acrylic acid (36) is obtained.

[Scheme 4]

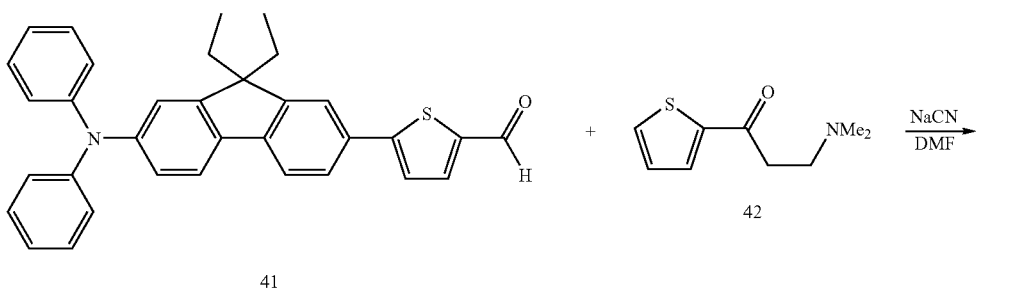

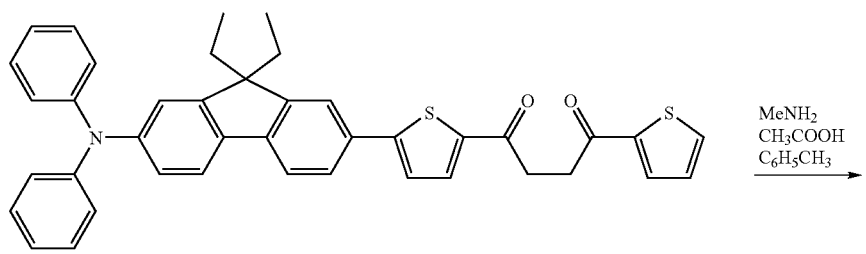

-continued

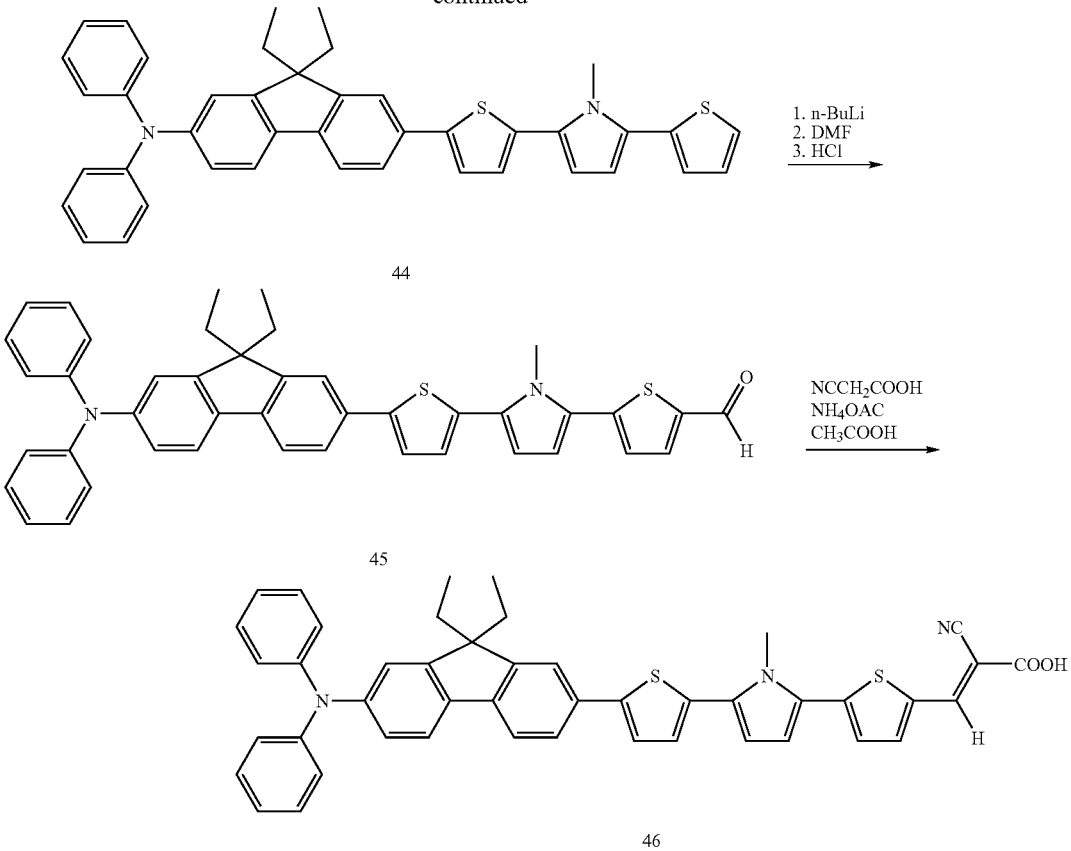

As shown in scheme 4, in the presence of sodium cyanide, 5-(7-diphenylamino-9,9-diethyl-9H-fluoren-2-yl)-thiophene-2-carbaldehyde (41) is reacted with 3-dimethylamino-1-(2-thienyl)-1-prapanone (42) to obtain 1-(5-(7-diphenylamino-9,9-diethyl-9H-fluoren-2-yl)thiophenyl-2-yl)-4-(thiophen-2-yl)-1,4-butanedione (43). Then, in the presence of acetic acid, 1-(5-(7-diphenylamino-9,9-diethyl-9H-fluoren-2-yl)thiophenyl-2-yl)-4-(thiophen-2-yl)-1,4-butanedione (43) is reacted with methylamine to obtain 9,9-diethyl-7-(5-(N-methyl-5-(thiophen-2-yl)pyrrol-2-yl)thiophen-2-yl)-N,N-diphenyl-9H-fluoren-2-amine (44). n-butyl lithium is reacted with 9,9-diethyl-7-(5-(N-methyl-5-(thiophen-2-yl)-pyrrol-2-yl)thiophen-2-yl)-N,N-diphenyl-9H-fluoren-2-amine (44), and then DMF is added thereto to obtain 5-(5-(5-(7-diphenylamino-9,9-diethyl-9H-fluoren-2-yl)thiophenyl-2-yl)-N-methyl-pyrrol-2-yl)thiophene-2-carbaldehyde (45). Finally, 5-(5-(5-(7-diphenylamino-9,9-diethyl-9H-fluoren-2-yl)thiophenyl-2-yl)-N-methyl-pyrrol-2-yl)thiophene-2-carbaldehyde (45) is reacted with cyanoacetic acid in acetic acid by using ammonium acetate as a catalyst, and (E)-2-cyano-3-(5-(5-(5-(7-diphenylamino-9,9-diethyl-9H-fluoren-2-yl)thiophenyl-2-yl)-N-methyl-pyrrol-2-yl)thiophene-2-yl)acrylic acid (46).

The following examples are intended for the purpose of illustration of the present invention. However, the scope of the present invention should be defined as the claims appended hereto, and the following examples should not be construed as in any way limiting the scope of the present invention. In the present invention, the molecule of the dye compound is presented in form of free acid. Nevertheless, the actual form of the dye compound of the present invention may be salt, and more likely, may be alkaline metal salt or quaternary ammonium salt. Without specific explanations, the unit of the parts and percentages used in the examples is calculated by weight and the temperature is represented by Celsius degrees (° C.).

Hereafter, the method for preparing the dye compound of the present invention is illustrated in detail with reference to above schemes 1 to 4.

EXAMPLE 1

Synthesis of 4-(1-methyl-1H-pyrrole-2-yl)-N,N-diphenylaniline)(12)

Under nitrogen atmosphere, 3.24 parts of 4-bromo-N,N-diphenyl-aniline (11), 4.00 parts of 1-methyl-2-(tributylstannyl)-1H-pyrrole which was synthesized according to the method illustrated in Armaroli, N.; Balzani, V. Angew. Chem. Int. Ed. 2007, 46, 52, and 0.07 parts of $PdCl_2(PPh_3)_2$ were added into dry dimethyl formamide under stirring to obtain a mixture. Then, the mixture was heated to 100° C. and reacted for 16 hours. After the mixture was cooled, a KF aqueous solution was used to stop the reaction. The mixture was extracted by diethyl ether, washed with a concentrated salt solution, and then dehydrated by magnesium sulfate. After removing the solvent, a product was purified by dichloromethane/hexane in a silica gel column to obtain the compound (12) of the present example.

EXAMPLE 2

Synthesis of 4-(5-(4-(diphenylamino)phenyl)-1-methyl-1H-pyrrol-2-yl)-benzaldehyde (14a)

The compound of the present example was synthesized by the same method as described in example 1, except that 1.85 parts of 4-bromo-benzaldehyde was used to substitute 4-bromo-N,N-diphenylaniline, and 6.63 parts of 4-(1-methyl-5-(tributylstannyl)-1H-pyrrole-2-yl)-N,N-diphenylaniline (13) was used to substitute 1-methyl-2-(tributylstannyl)-1H-pyrrole, wherein 4-(1-methyl-5-(tributylstannyl)-1H-pyrrole-2-yl)-N,N-diphenylaniline (13) was synthesized according to the method illustrated in Armaroli, N.; Balzani, V. *Angew. Chem. Int. Ed.* 2007, 46, 52.

EXAMPLE 3

Synthesis of (E)-2-cyano-3-[4-(5-(4-(diphenylamino)phenyl)-1-methyl-1H-pyrrol-2-yl)]phenyl)acrylic acid (15a)

0.80 parts of 4-(5-(4-(diphenylamino)phenyl)-1-methyl-1H-pyrrol-2-yl)benzaldehyde (14a), 0.21 parts of cyanoacetic acid, and 0.04 parts of ammonium acetate was added into 10 parts of acetic acid under stirring to obtain a mixture. Then, the mixture was heated to 120° C. and reacted for 8 hours. After the mixture was cooled to 25° C., the resultant solid was taken out. The resultant solid was washed by water, diethyl ether, and methanol sequentially to obtain a dark brown solid. Finally, the dark brown solid was purified in a silica gel column to obtain the compound (15a) of the present example.

EXAMPLE 4

Synthesis of 5-(5-(4-(diphenylamino)phenyl)-1-methyl-1H-pyrrol-2-yl)-thiophene-2-carbaldehyde (14b)

The compound of the present example was synthesized by the same method as described in example 2, except that 1.91 parts of 5-bromo-2-thiophene carboxaldehyde was used to substitute 4-bromobenzaldehyde.

EXAMPLE 5

Synthesis of (E)-2-cyano-3-(5-(5-(4-(diphenylamino)phenyl)-1-methyl-1H-pyrrol-2-yl)thiophen-2-yl)acrylic acid (15b)

The compound of the present example was synthesized by the same method as described in example 3, except that 0.81 parts of 5-(5-(4-(diphenylamino)phenyl)-1-methyl-1H-pyrrol-2-yl)-thiophene-2-carbaldehyde (14b) was used to substitute 4-(5-(4-(diphenylamino)phenyl)-1-methyl-1H-pyrrol-2-yl)benzaldehyde (14a).

EXAMPLE 6

Synthesis of 2-(7-bromo-9,9-diethyl-9H-fluoren-2-yl)-1-methyl-1H-pyrrole (22)

The compound of the present example was synthesized by the same method as described in example 1, except that 3.80 parts of 2,7-dibromo-9,9-diethyl-9H-fluorene (21) was used to substitute 4-bromo-N,N-diphenylaniline.

EXAMPLE 7

Synthesis of 9,9-diethyl-7-(1-methyl-1H-pyrrol-2-yl)-N,N-diphenyl-9H-fluoren-2-amine (23a)

3.00 parts of 2-(7-bromo-9,9-diethyl-9H-fluoren-2-yl)-1-methyl-1H-pyrrole (22), 1.54 parts of diphenylamine, 1.14 parts of sodium tert-butoxide, 0.09 parts of Pd(dba)$_2$, and 0.065 parts of tri-tert-butyl phosphine were added into 50 parts of toluene under stirring to obtain a mixture. Then, the mixture was heated to 80° C. and reacted for 8 hours. After the reaction was stopped by water, a product was extracted by diethyl ether, and then dehydrated by magnesium sulfate. After the solvent was removed, the product was purified by dichloromethane/hexane in a silica gel column to obtain the compound (23a) of the present example.

EXAMPLE 8

Synthesis of 5-[N-methyl-2-(7-diphenylamino-9,9-diethyl-9H-fluoren-2-yl)pyrrol-5-yl]thiophene-2-carbaldehyde (25a)

The compound of the present example was synthesized by the same method as described in example 4, except that 8.18 parts of N-methyl-2-(7-diphenylamino-9,9-diethyl-9H-fluoren-2-yl)-5-tributyl-stannylpyrrole (24a) was used to substitute 4-(1-methyl-5-(tributylstannyl)-1H-pyrrole-2-yl)-N,N-diphenylaniline, wherein N-methyl-2-(7-diphenylamino-9,9-diethyl-9H-fluoren-2-yl)-5-tributyl-stannylpyrrole (24a) was synthesized according to the method illustrated in Armaroli, N.; Balzani, V. *Angew. Chem. Int. Ed.* 2007, 46, 52.

EXAMPLE 9

Synthesis of (E)-2-cyano-3-[5-(N-methyl-2-(7-diphenylamino-9,9-diethyl-9H-fluoren-2-yl)pyrrol-5-yl)thiophen-2-yl]acrylic acid (26a)

The compound of the present example was synthesized by the same method as described in example 3, except that 1.08 parts of 5-[N-methyl-2-(7-diphenylamino-9,9-diethyl-9H-fluoren-2-yl)pyrrol-5-yl]thiophene-2-carbaldehyde (25a) was used to substitute 4-(5-(4-(diphenylamino)phenyl)-1-methyl-1H-pyrrol-2-yl)benzaldehyde (14a).

EXAMPLE 10

Synthesis of N-methyl-2-(7-(N-phenyl-1-naphthylamino)-9,9-diethyl-9H-fluoren-2-yl)pyrrole (23b)

The compound of the present example was synthesized by the same method as described in example 7, except that 2.0 parts of N-phenyl-1-naphthylamine was used to substitute diphenylamine.

EXAMPLE 11

Synthesis of 5-[N-methyl-2-(7-(N-phenyl-1-naphthylamino)-9,9-diethyl-9H-fluoren-2-yl)pyrrol-5-yl]thiophene-2-carbaldehyde (25b)

The compound of the present example was synthesized by the same method as described in example 4, except that 8.72 parts of N-methyl-2-(7-(N-phenyl-1-naphthylamino)-9,9-diethyl-9H-fluoren-2-yl)-5-tributyl-stannylpyrrole (24b) was used to substitute 4-(1-methyl-5-(tributyl stannyl)-1H-pyrrole-2-yl)-N,N-diphenylaniline, wherein N-methyl-2-(7-(N-phenyl-1-naphthylamino)-9,9-diethyl-9H-fluoren-2-yl)-5-tributyl-stannylpyrrole (24b) was synthesized according to the method illustrated in Armaroli, N.; Balzani, V. *Angew. Chem. Int. Ed.* 2007, 46, 52.

EXAMPLE 12

Synthesis of (E)-2-cyano-3-[5-(N-methyl-2-(7-(N-phenyl-1-naphthyl-amino)-9,9-diethyl-9H-fluoren-2-yl)pyrrol-5-yl)thiophen-2-yl]acrylic acid (26b)

The compound of the present example was synthesized by the same method as described in example 3, except that 1.17 parts of 5-[N-methyl-2-(7-(N-phenyl-1-naphthylamino)-9,9-diethyl-9H-fluoren-2-yl)pyrrol-5-yl]thiophene-2-carbaldehyde (25b) was used to substitute 4-(5-(4-(diphenylamino)phenyl)-1-methyl-1H-pyrrol-2-yl)benzaldehyde.

EXAMPLE 13

Synthesis of N-methyl-2-(3-bromo-9-hexyl-9H-carbazol-6-yl)pyrrole (32)

The compound of the present example was synthesized by the same method as described in example 1, except that 4.09 parts of 3,6-dibromo-9-hexyl-9H-carbazole (31) was used to substitute 4-bromo-N,N-diphenyl aniline.

EXAMPLE 14

Synthesis of N-methyl-2-(3-diphenylamino-9-hexyl-9H-carbazol-6-yl)pyrrole (33)

The compound of the present example was synthesized by the same method as described in example 7, except that 3.23 parts of N-methyl-2-(3-bromo-9-hexyl-9H-carbazol-6-yl)pyrrole (32) was used to substitute 2-(7-bromo-9,9-diethyl-9H-fluoren-2-yl)-1-methyl-1H-pyrrole.

EXAMPLE 15

Synthesis of 5-[N-methyl-2-(3-diphenylamino-9-hexyl-9H-carbazol-6-yl)-pyrrol-5-yl]thiophene-2-carbaldehyde (35)

The compound of the present example was synthesized by the same method as described in example 4, except that 8.50 parts of N-methyl-2-(3-diphenylamino-9-hexyl-9H-carbazol-6-yl)-5-tributyl-stannylpyrrol (34) was used to substitute 4-(1-methyl-5-(tributyl stannyl)-1H-pyrrole-2-yl)-N,N-diphenylaniline, wherein N-methyl-2-(3-diphenyl-amino-9-hexyl-9H-carbazol-6-yl)-5-tributylstannylpyrrol (34) was synthesized according to the method illustrated in Armaroli, N.; Balzani, V. *Angew. Chem. Int. Ed.* 2007, 46, 52.

EXAMPLE 16

Synthesis of (E)-2-cyano-3-[5-(N-methyl-2-(3-diphenylamino-9-hexyl-9H-carbazol-6-yl)pyrrol-5-yl)thiophen-2-yl]acrylic acid (36)

The compound of the present example was synthesized by the same method as described in example 3, except that 1.13 parts of 5-[N-methyl-2-(3-diphenylamino-9-hexyl-9H-carbazol-6-yl)-pyrrol-5-yl]thiophene-2-carbaldehyde (35) was used to substitute 4-(5-(4-(diphenylamino)phenyl)-1-methyl-1H-pyrrol-2-yl)benzaldehyde.

EXAMPLE 17

Synthesis of 1-(5-(7-diphenylamino-9,9-diethyl-9H-fluoren-2-yl)-thiophenyl-2-yl)-4-(thiophen-2-yl)-1,4-butanedione (43)

Under nitrogen atmosphere, 0.12 parts of ground sodium cyanide was mixed with 1.00 part of dimethyl formamide, and then 1.20 parts of 5-(7-diphenylamino-9,9-diethyl-9H-fluoren-2-yl)thiophene-2-carbaldehyde (41) dissolved in 5.00 parst of dimethyl formamide was added thereto to obtain a mixture. After stirring for 10 minutes, 0.44 parts of 3-dimethylamino-1-(2-thienyl)-1-prapanone (42) dissolved in 5.00 parts of dimethyl formamide was added to the mixture slowly within 10 minutes. After the dark red mixture was reacted for 16 hours, the dark red mixture was added into 100 parts of water and then extracted with dichloromethane. The combined extraction solution was washed by 40 parts of 10% HCl, 40 parts of saturated aqueous NaHCO$_3$, and 50 parts of water sequentially, and then dehydrated by magnesium sulfate. After removing the solvent, a product was purified by dichloromethane/hexane in a silica gel column to obtain the compound (43) of the present example.

EXAMPLE 18

Synthesis of 9,9-diethyl-7-(5-(N-methyl-5-(thiophen-2-yl)pyrrol-2-yl) thiophen-2-yl)-N,N-diphenyl-9H-fluoren-2-amine (44)

Under nitrogen atmosphere, a mixture solution, comprising 0.94 parts of 1-(5-(7-diphenylamino-9,9-diethyl-9H-fluoren-2-yl)-thiophenyl-2-yl)-4-(thiophen-2-yl)-1,4-butanedione (43), 0.27 parts of 40% methylamine aqueous solution, 0.20 parts of glacial acetic acid, and 30 parts of toluene, was added in a reaction flask fitted with a Dean-Stark trap, and a reflux reaction was performed for 48 hours. The mixture solution was washed with water, and then the organic layer was concentrated under vacuum to obtain a residue. The residue was dissolved by dichloromethane, washed with saturated aqueous NaHCO$_3$, water, and concentrated salt solution sequentially, and then dehydrated by magnesium sulfate. After removing the solvent, a product was purified by dichloromethane/hexane in a silica gel column to obtain the compound (44) of the present example.

EXAMPLE 19

Synthesis of 5-(5-(5-(7-diphenylamino-9,9-diethyl-9H-fluoren-2-yl)thiophenyl-2-yl)-N-methyl-pyrrol-2-yl)thiophene-2-carbaldehyde (45)

Under nitrogen atmosphere, a mixture solution, comprising 0.40 parts of 9,9-diethyl-7-(5-(N-methyl-5-(thiophen-2-yl)pyrrol-2-yl)thiophen-2-yl)-N,N-diphenyl-9H-fluoren-2-amine (44) and tetrahydrofuran (THF), was cooled to −78° C. by using acetone-liquid N$_2$ bath. 0.40 parts of hexane solution of n-butyl lithium (1.6 M) was added into the mixture solution drop by drop within 10 minutes under severe stirring. The mixture was heated to 0° C. within 1 hour, and then kept in 0° C. for 1 hour. Then, the mixture was cooled to −78° C., and dichloromethane was added thereto. The temperature of the mixture was recovered to 25° C., and the mixture was stirred for 16 hours. The reaction was stopped by using 1 N HCl, and then the product was extracted by diethyl ether, and the combined extraction solution was dehydrated by magnesium sulfate. After removing the solvent, the product was purified by dichloromethane/hexane in a silica gel column to obtain the compound (45) of the present example.

EXAMPLE 20

Synthesis of (E)-2-cyano-3-(5-(5-(5-(7-diphenylamino-9,9-diethyl-9H-fluoren-2-yl)thiophenyl-2-yl)-N-methyl-pyrrol-2-yl)thiophene-2-yl)acrylic acid (46)

The compound of the present example was synthesized by the same method as described in example 3, except that 1.23 parts of 5-(5-(5-(7-diphenylamino-9,9-diethyl-9H-fluoren-2-yl)thiophenyl-2-yl)-N-methyl-pyrrol-2-yl)thiophene-2-carbaldehyde (45) was used to substitute 4-(5-(4-(diphenylamino)phenyl)-1-methyl-1H-pyrrol-2-yl)benzaldehyde.

Testing Methods and Results

UV-Vis Spectrum

Using dimethyl formamide as a solvent, the dye compounds synthesized in example 3, example 5, example 9, example 12, and example 20 of the present invention were formulated into dye solutions in the concentration of $1.0 \times 10^{-5}$ M. In addition, using dimethyl formamide as a solvent, the dye compound synthesized in example 16 of the present invention and the N719 dye were formulated into dye solutions in the concentration of $2.0 \times 10^{-5}$ M. Then, the UV-Vis spectra of the dye solutions above-mentioned were measured.

Manufacture and Test of the Dye-Sensitized Solar Cell

An electrode prepared by $TiO_2$ nano crystalline particles was soaked in a solution comprising the dye compound of the present invention for a period of time, and the dye compound would adhered to the $TiO_2$ nano crystalline particles of the electrode. The electrode with $TiO_2$ nano crystalline particles was taken out, washed slightly with a solvent, and dried, and then the electrode was covered with a counterelectrode and sealed up. After that, an electrolyte (acetonitrile solution of 0.05 M $I_2$/0.5M LiI/0.5 M t-butyl pyridine) was added therein, and the injection opening was sealed up to obtain a dye-sensitized solar cell with effective area of 0.25 cm². The short circuit current ($J_{SC}$), open circuit voltage ($V_{OC}$), photoelectric conversion efficiency (η), filling factor (FF), and incident photon-to-current conversion efficiency (IPCE) of the resulted dye-sensitized solar cell were measured under the illumination of AM 1.5 stimulated light.

COMPARATIVE EXAMPLE

A dye-sensitized solar cell prepared with N719 dye was produced by the same method as described above. Besides, the short circuit current ($J_{SC}$), open circuit voltage ($V_{OC}$), photoelectric conversion efficiency (η), filling factor (FF), and incident photon-to-current conversion efficiency (IPCE) of the dye-sensitized solar cell with N719 dye were also measured under the illumination of AM 1.5 stimulated light.

The testing results are shown in the following Table 1:

TABLE 1

Testing results of the dye and the dye-sensitized solar cell

| | dye | Molar absorption coefficient of the longest absorption wavelength ($M^{-1}cm^{-1}$) | $J_{SC}$ ($mA/cm^2$) | $V_{OC}$ (V) | FF | η (%) |
|---|---|---|---|---|---|---|
| Eaxmple 3 | 15a | 53900 | 13.47 | 0.60 | 0.59 | 4.77 |
| Eaxmple 5 | 15b | 45600 | 14.20 | 0.57 | 0.60 | 4.79 |
| Eaxmple 9 | 26a | 70900 | 18.14 | 0.61 | 0.56 | 6.16 |
| Eaxmple 12 | 26b | 73800 | 16.79 | 0.64 | 0.58 | 6.18 |
| Eaxmple 16 | 36 | 27100 | 12.93 | 0.58 | 0.64 | 4.80 |
| Eaxmple 20 | 46 | 97000 | 13.54 | 0.60 | 0.64 | 5.25 |
| Comparative example | N719 | 12600 | 16.08 | 0.72 | 0.63 | 7.19 |

The testing results of Table 1 show that the molar absorption coefficient of the longest absorption wavelength of the dye compounds of the present invention are higher than the molar absorption coefficient of the longest absorption wavelength of the N719 dye. It means that the dye compounds of the present invention can achieve the same absorption efficiency as the N719 dye with fewer using amount.

In conclusion, the present invention is different from the prior arts in several ways, such as in purposes, methods and efficiency, or even in technology and research and design. Although the present invention has been explained in relation to its preferred embodiment, it is to be understood that many other possible modifications and variations can be made without departing from the scope of the invention as hereinafter claimed. Hence, the scope of the present invention should be defined as the claims appended hereto, and the foregoing examples should not be construed as in any way limiting the scope of the present invention.

What is claimed is:

1. A dye compound, which is represented by the following formula (I):

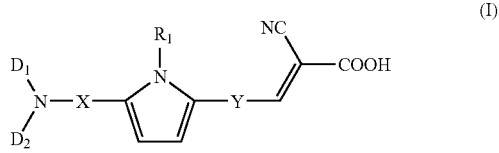

wherein $R_1$ is $C_{1\sim6}$ alkyl;

$D_1$, and $D_2$ are each independently $C_{1\sim6}$ alkyl,

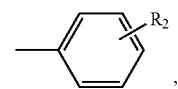

Y is

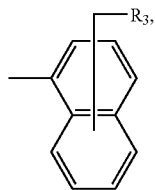

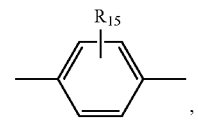

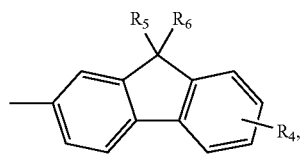

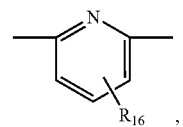

or

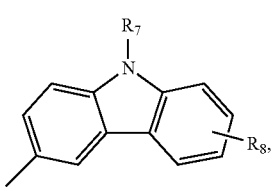

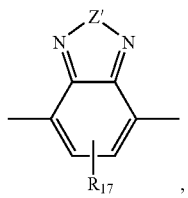

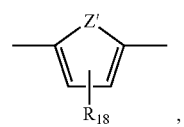

wherein R$_2$, R$_3$, R$_4$, and R$_8$ are each independently H, C$_{1\sim6}$ alkyl, C$_{1\sim6}$ alkoxy, amino, or halogen, R$_5$, and R$_6$ are each independently H, C$_{1\sim6}$ alkyl, C$_{1\sim6}$ alkoxy, or halogen, and R$_7$ is H, or C$_{1\sim6}$ alkyl;

X is,

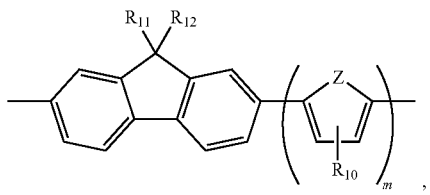

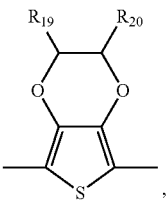

or

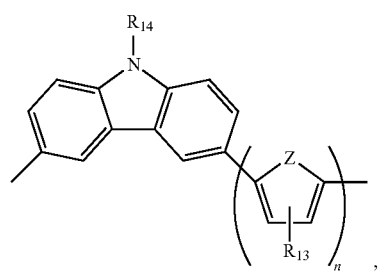

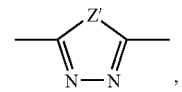

wherein R$_{15}$, R$_{16}$, and R$_{17}$ are each independently H, C$_{1\sim6}$ alkyl, C$_{1\sim6}$ alkoxy, or halogen, R$_{18}$, R$_{19}$, and R$_{20}$ are each independently H, or C$_{1\sim6}$ alkyl, and Z' is O, S, or Se.

2. The dye compound according to claim 1, wherein D$_1$, and D$_2$ are each independently

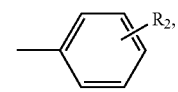

wherein R$_{11}$ and R$_{12}$ are each independently H, C$_{1\sim6}$ alkyl, C$_{1\sim6}$ alkoxy, or halogen, R$_{10}$, R$_{13}$, and R$_{14}$ are each independently H, or C$_{1\sim6}$ alkyl, Z is O, S, or Se, m is 0, or 1, and n is 0, or 1;

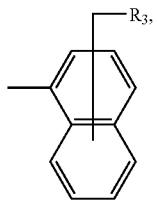

or

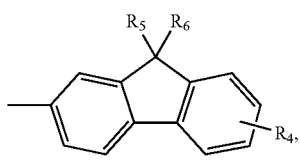

or

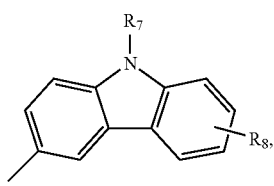

wherein $R_2$, $R_3$, $R_4$, $R_5$, $R_6$, and $R_8$ are each independently H, $C_{1\sim6}$ alkyl, $C_{1\sim6}$ alkoxy, or halogen, and $R_7$ is $C_{1\sim6}$ alkyl.

3. The dye compound according to claim 1, wherein $D_1$, and $D_2$ are each independently

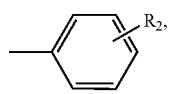

or

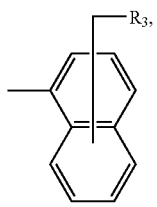

wherein $R_2$, and $R_3$ are each independently H, $C_{1\sim6}$ alkyl, $C_{1\sim6}$ alkoxy, amino, or halogen.

4. The dye compound according to claim 3, wherein $R_2$, and $R_3$ are H.

5. The dye compound according to claim 1, wherein Z is S, m is 0, or 1, and n is 0.

6. The dye compound according to claim 5, wherein $R_{11}$, $R_{12}$, and $R_{14}$ are each independently H, or $C_{1\sim6}$ alkyl.

7. The dye compound according to claim 6, wherein $R_{10}$ is H.

8. The dye compound according to claim 1, wherein Y is

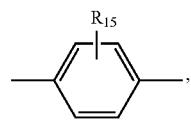

or

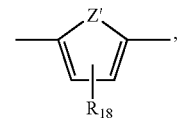

wherein $R_{15}$ is H, $C_{1\sim6}$ alkyl, $C_{1\sim6}$ alkoxy, or halogen, $R_{18}$ is H, or $C_{1\sim6}$ alkyl, and Z' is O, S, or Se.

9. The dye compound according to claim 8, wherein Z' is S.

10. The dye compound according to claim 9, wherein $D_1$, and $D_2$ are each independently

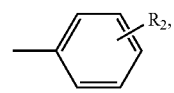

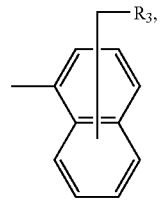

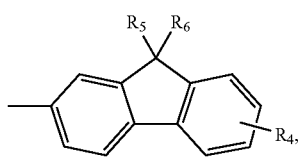

or

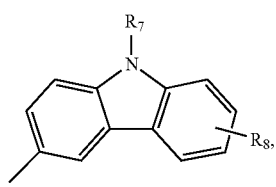

wherein $R_2$, $R_3$, $R_4$, $R_5$, $R_6$, and $R_8$ are each independently H, $C_{1\sim6}$ alkyl, $C_{1\sim6}$ alkoxy, or halogen, and $R_7$ is $C_{1\sim6}$ alkyl.

11. The dye compound according to claim 10, wherein Z is S, m is 0, or 1, and n is 0.

12. The dye compound according to claim 11, wherein $R_{15}$, and $R_{18}$ are H.

13. The dye compound according to claim 9, wherein $D_1$, and $D_2$ are each independently

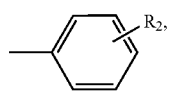

or

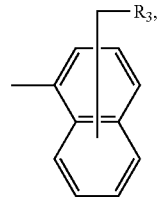

wherein $R_2$, and $R_3$ are each independently H, $C_{1\sim6}$ alkyl, $C_{1\sim6}$ alkoxy, amino, or halogen.

14. The dye compound according to claim 13, wherein $R_2$, and $R_3$ are H.

15. The dye compound according to claim 14, wherein Z is S, m is 0, or 1, and n is 0.

16. The dye compound according to claim 15, wherein $R_{15}$, and $R_{18}$ are H.

17. A dye compound, which is represented by the following formulas (26a), (26b), (36), or (46):

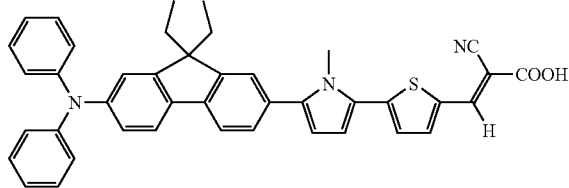

(26a)

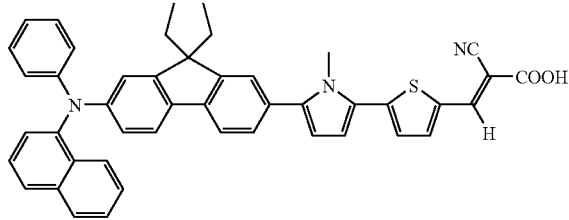

(26b)

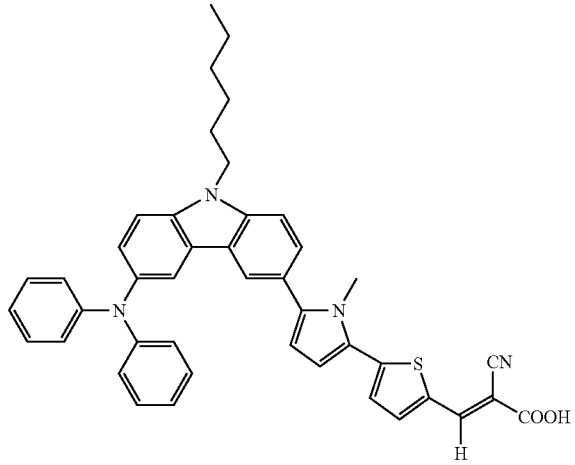

(36)

-continued
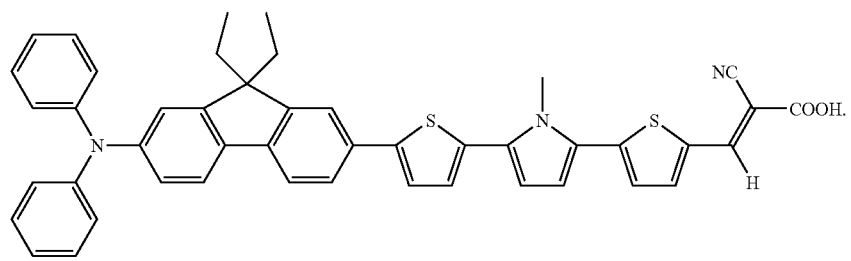
(46)
* * * * *